(12) United States Patent
Foster et al.

(10) Patent No.: US 7,942,152 B1
(45) Date of Patent: May 17, 2011

(54) SOFT HAND RESTRAINT DEVICE FOR TRANSPORTING PRISONERS

(76) Inventors: John Thomas Foster, Westerville, OH (US); Glenda Louise Hill-Foster, Westerville, OH (US)

( * ) Notice: Subject to any disclaimer, the term of this patent is extended or adjusted under 35 U.S.C. 154(b) by 0 days.

(21) Appl. No.: 12/062,519

(22) Filed: Apr. 4, 2008

Related U.S. Application Data

(63) Continuation-in-part of application No. 10/952,586, filed on Sep. 26, 2004, now abandoned.

(60) Provisional application No. 60/543,185, filed on Feb. 10, 2004.

(51) Int. Cl.
*A61F 5/37* (2006.01)

(52) U.S. Cl. ......... 128/879; 128/878; 128/869; 119/770

(58) Field of Classification Search .................. 128/869, 128/878, 879; 119/769, 770, 792, 816, 819
See application file for complete search history.

(56) References Cited

U.S. PATENT DOCUMENTS

| | | | |
|---|---|---|---|
| 458,888 A * | 9/1891 | Eisele ............................. 441/57 |
| 3,740,977 A | 6/1973 | Stefansen et al. |
| 3,741,207 A | 6/1973 | Fuson |
| 4,469,096 A * | 9/1984 | Rivadeneyra ................. 128/879 |
| 4,618,328 A | 10/1986 | Chi |
| 4,887,616 A | 12/1989 | Baijnath |
| 4,964,419 A | 10/1990 | Karriker |
| 5,007,257 A | 4/1991 | Thompson |
| 5,031,641 A * | 7/1991 | Upton ........................... 128/879 |
| 5,088,158 A | 2/1992 | Burkholder |
| 5,121,743 A | 6/1992 | Bishop |
| 5,159,728 A | 11/1992 | Bingold |
| 5,261,728 A | 11/1993 | Carmichael |
| 5,289,164 A * | 2/1994 | Novak ........................... 340/574 |
| D347,156 S | 5/1994 | Starett et al. |
| 5,345,947 A | 9/1994 | Fisher |
| 5,349,966 A * | 9/1994 | Garcia ........................... 128/879 |
| D352,572 S | 11/1994 | Pustizzi, Jr. |
| 5,377,510 A | 1/1995 | Smith |
| 5,398,383 A | 3/1995 | Bingold |
| 5,479,943 A | 1/1996 | Kushnell, III |
| 5,542,433 A | 8/1996 | Saupe |
| 5,555,751 A | 9/1996 | Strickland |
| 5,604,933 A | 2/1997 | Stephens |
| 5,732,576 A | 3/1998 | Moore |
| 5,797,404 A | 8/1998 | Stanchin, II |
| 6,000,249 A | 12/1999 | Wilber |
| 6,138,677 A | 10/2000 | DeVane |
| 6,886,374 B2 | 5/2005 | Clifton, Jr. |
| 7,210,172 B2 | 5/2007 | Adams, Jr. |

\* cited by examiner

*Primary Examiner* — Patricia M Bianco
*Assistant Examiner* — Camtu T Nguyen
(74) *Attorney, Agent, or Firm* — Raymond N. Ervin, Ltd.

(57) ABSTRACT

The present invention, a SOFT HAND RESTRAINT DEVICE FOR TRANSPORTING PRISONERS comprising a fabric pouch, a retaining clip mechanism, a wrist retaining strap, restraint grommets, a handcuff retainer and a splay device seeks to provide law enforcement personnel a means of safely transporting prisoners, whereby the ability of a prisoner to grasp objects or persons and exercise his hands in an offensive posture is temporarily debilitated. This is accomplished by maintaining the hand in a position whereby the middle and ring finger are splayed apart at a predetermined distance by a splay device, which interferes with the grip ergonomics, wherein the prisoner is unable to exert sufficient force to overcome the splay device and hence is unable to form a grip. Additional embodiments providing differing arrangements of the primary elements are also disclosed and claimed.

11 Claims, 9 Drawing Sheets

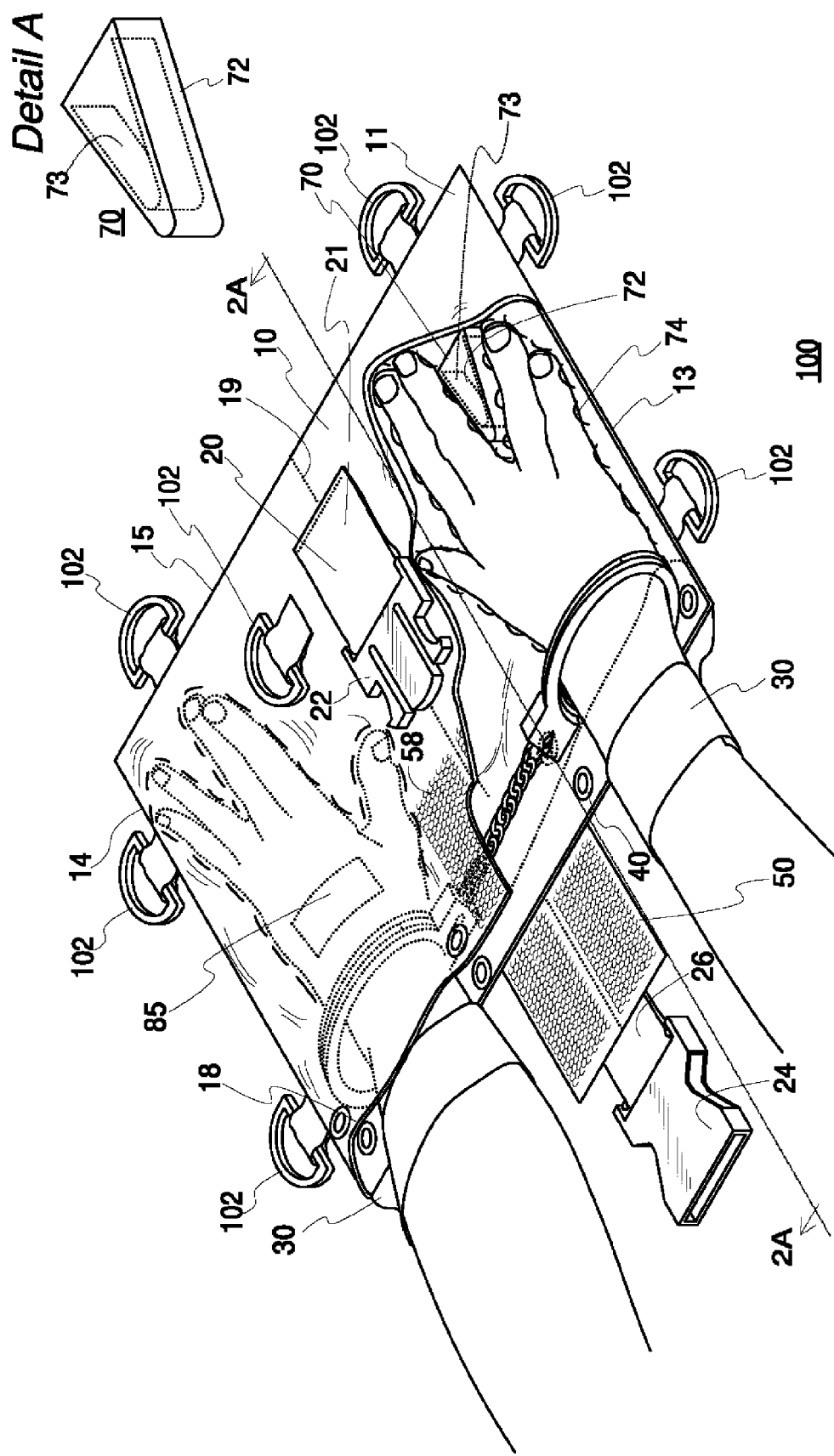

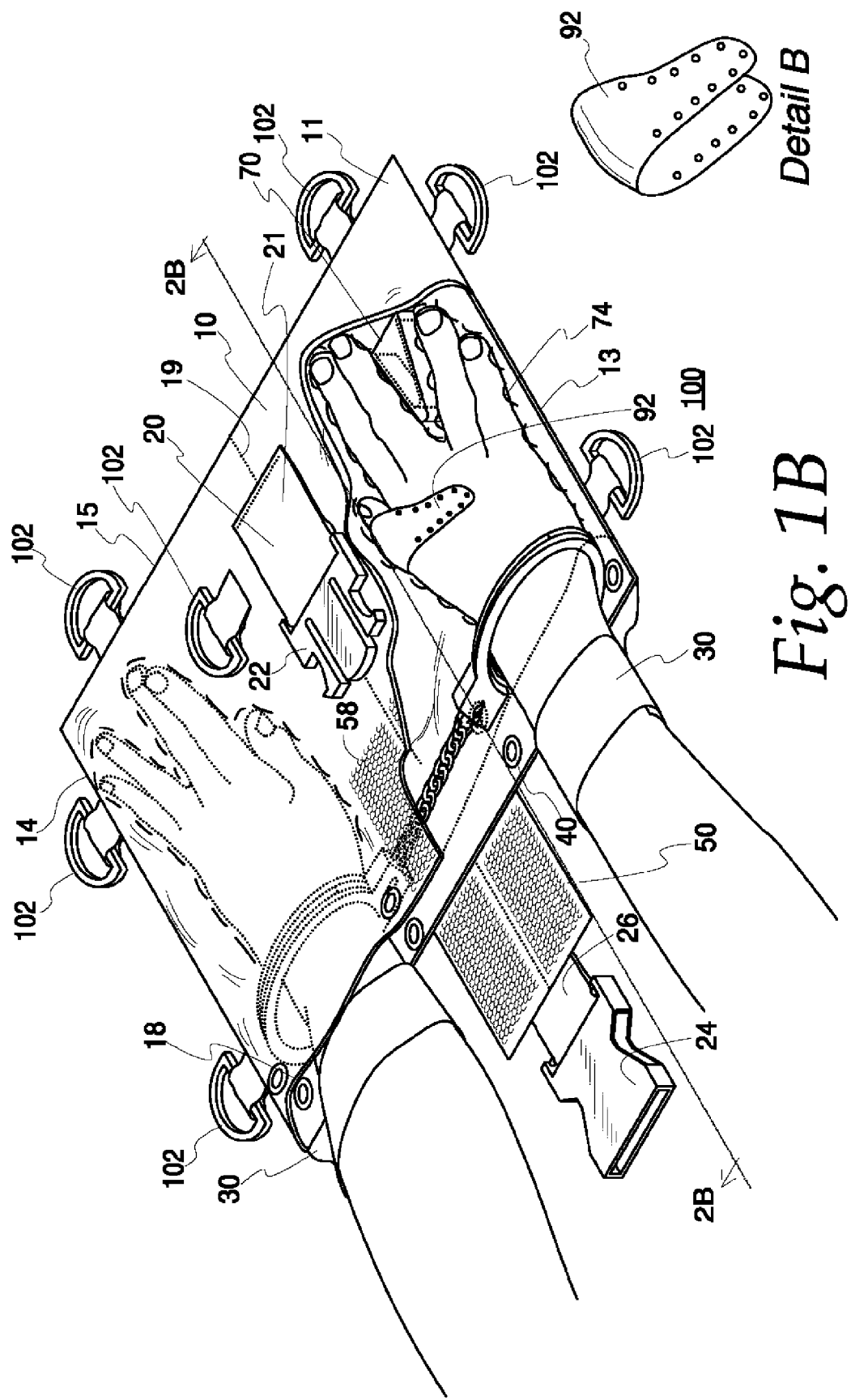

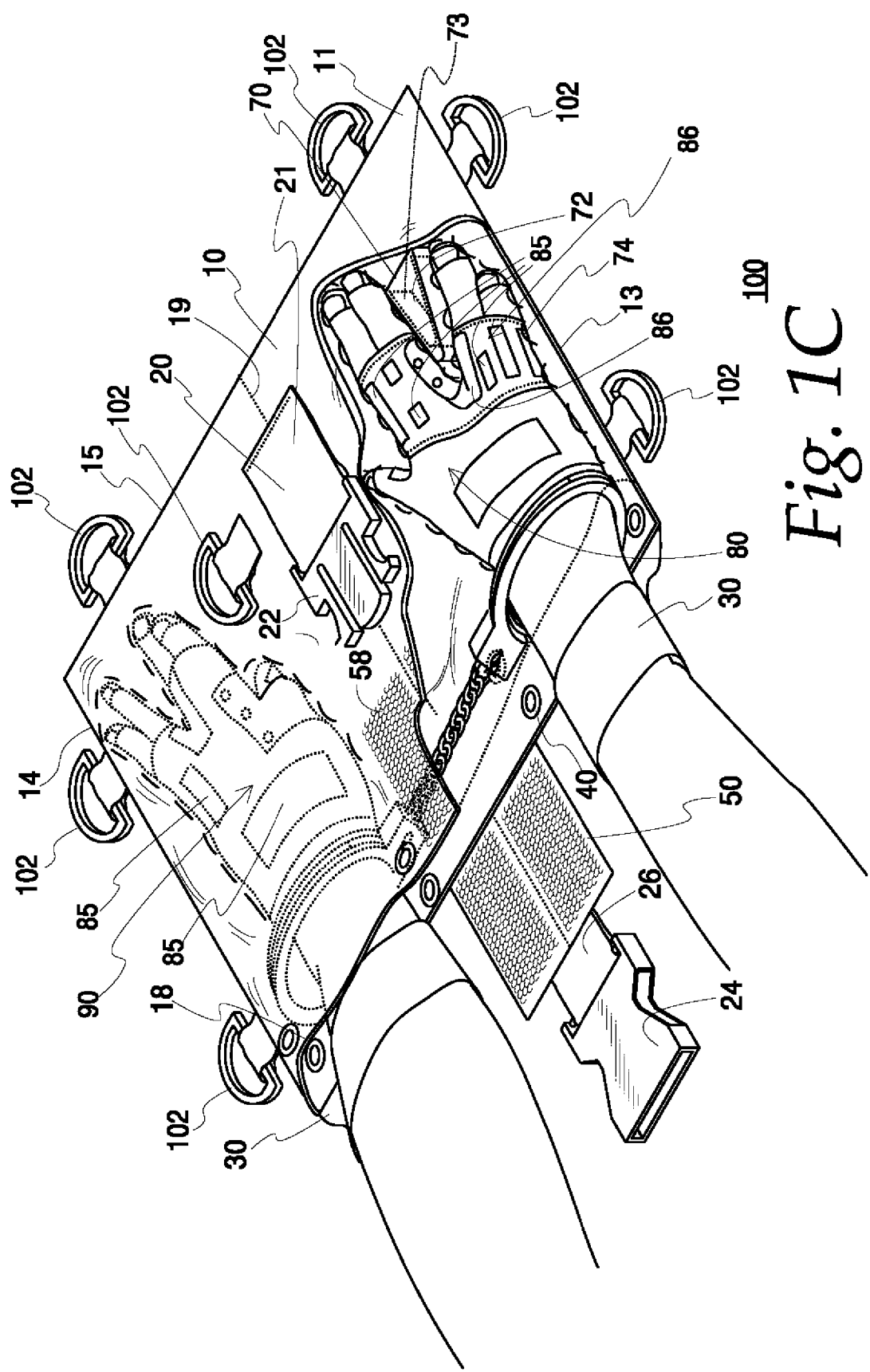

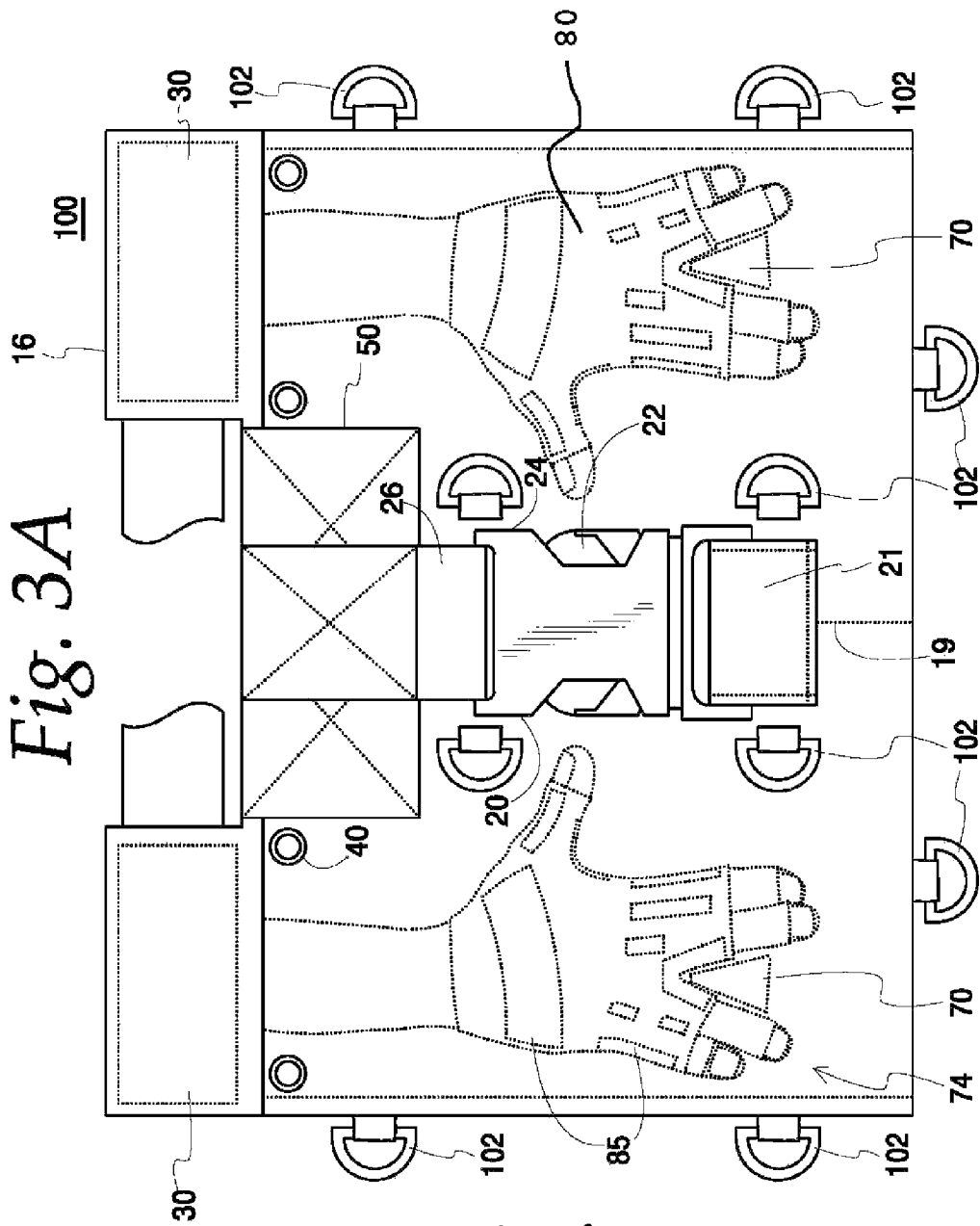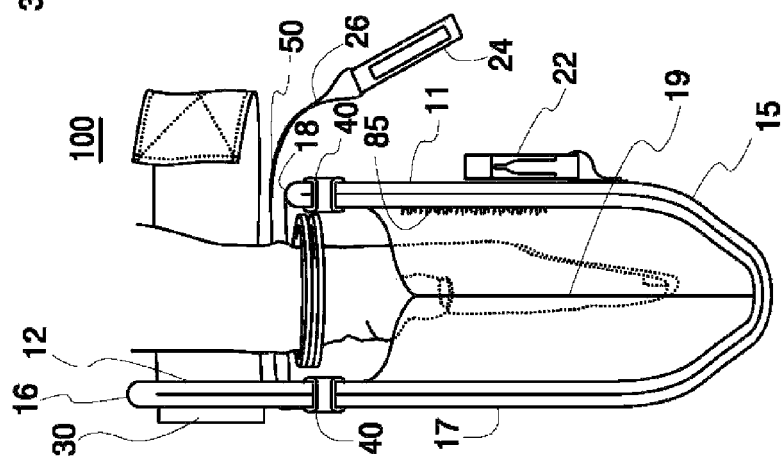

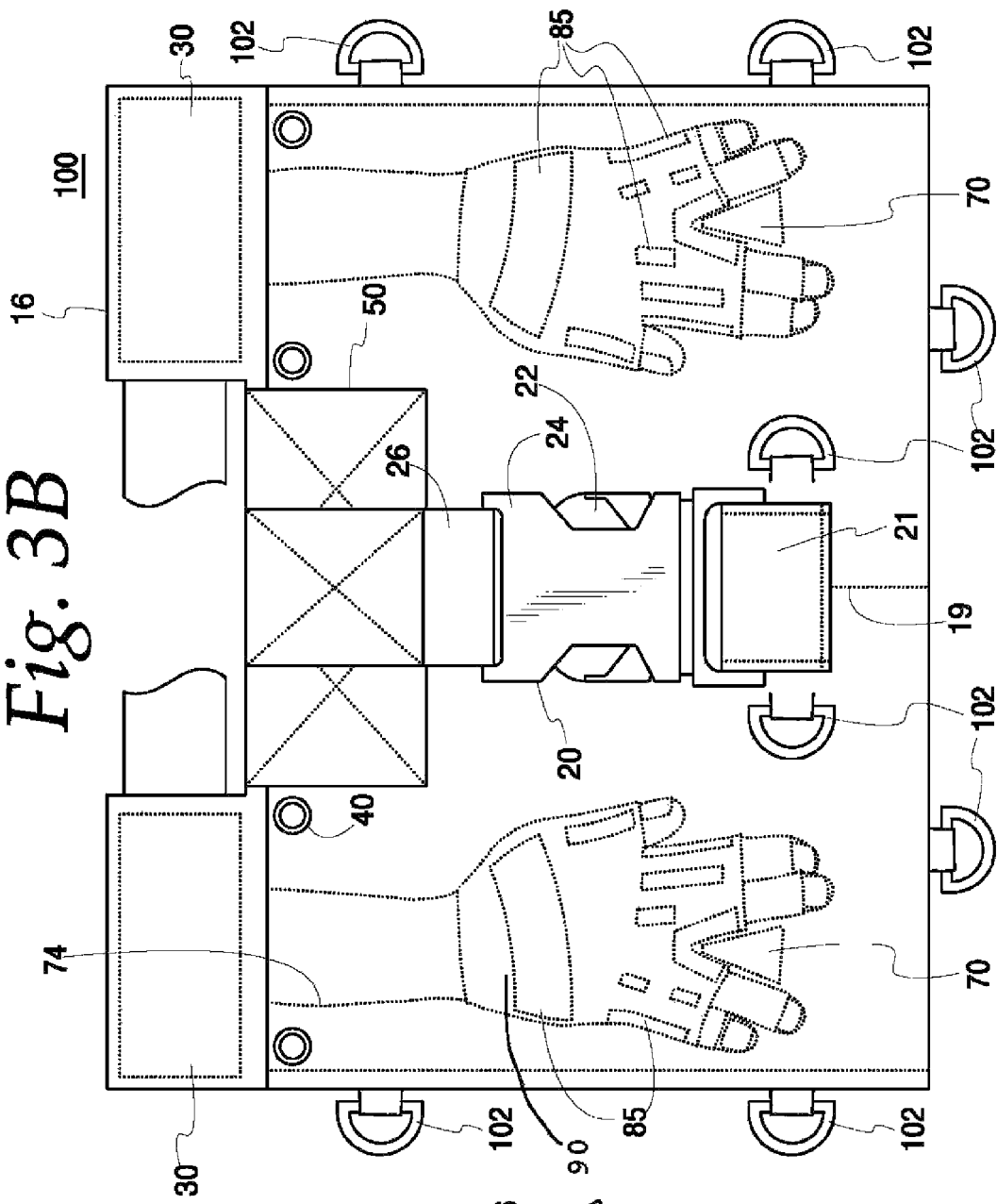
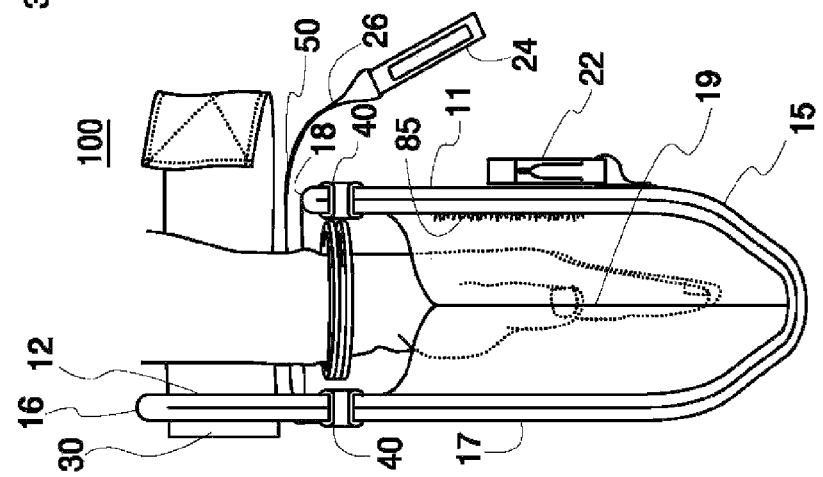

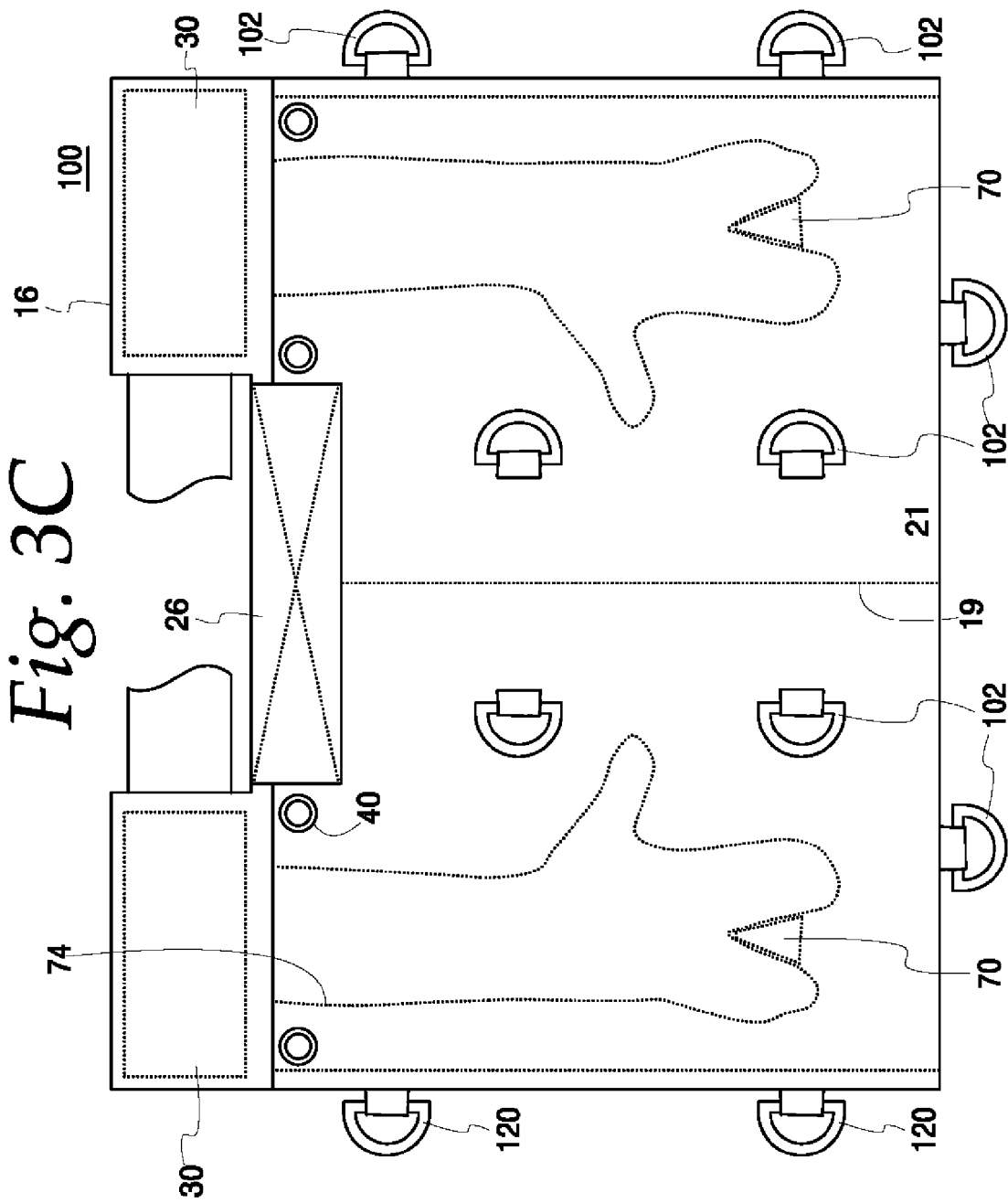

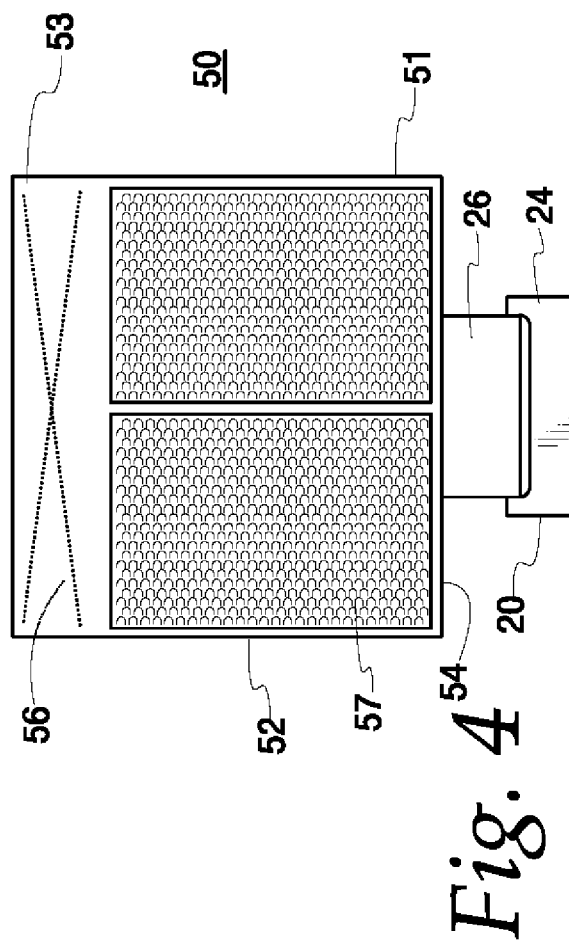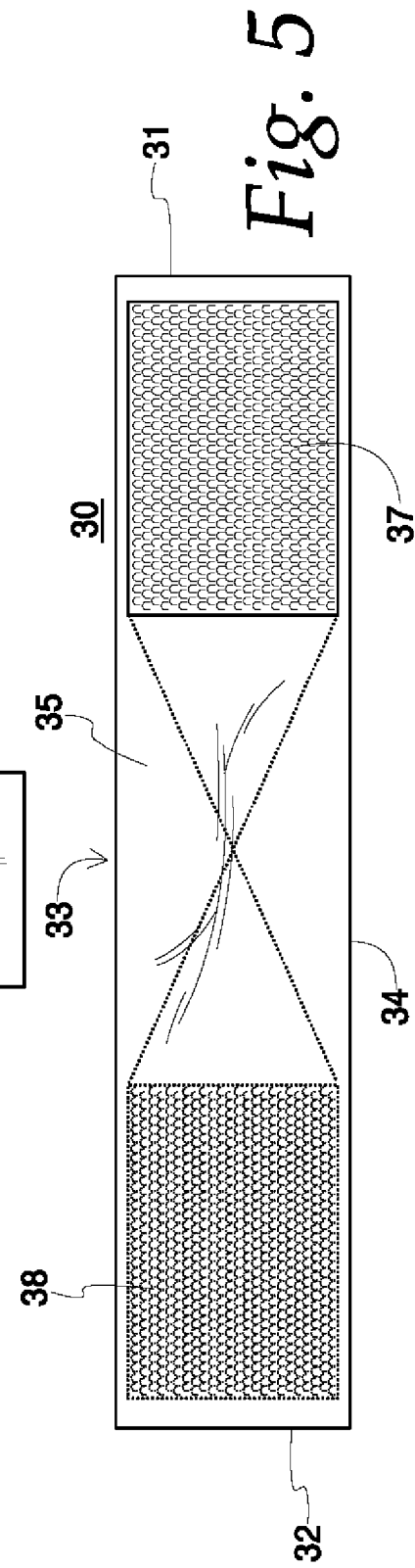

SOFT HAND RESTRAINT DEVICE FOR TRANSPORTING PRISONERS

CLAIM FOR PRIORITY OF INVENTION

This application claims the benefit of U.S. Non-Provisional application Ser. No. 11/401,813, Kufbag Restraining Device, filed 10 Apr. 2006, presently abandoned, in accordance with 35 USC §120; which claims the benefit of U.S. Non-Provisional application Ser. No. 10/952,586, Soft Hand Restraint Device for Transporting Prisoners (formerly, Kufbag Restraint Device for Transporting Prisoners), filed 26 Sep. 2004, presently abandoned, in accordance with 35 USC §120; which claims the benefit of U.S. Provisional Application No. 60/543,185, Kufbag Restraint for Transporting Prisoners, filed 10 Feb. 2004 presently abandoned, in accordance with 35 USC §119 (e).

CROSS-REFERENCE TO RELATED APPLICATIONS

This application claims the benefit of U.S. Non-Provisional application Ser. No. 11/401,813, Kufbag Restraining Device, filed 10 Apr. 2006, presently abandoned, which claims the benefit of U.S. Non-Provisional application Ser. No. 10/952,586, Soft Hand Restraint Device for Transporting Prisoners (formerly, Kufbag Restraint Device for Transporting Prisoners), filed 26 Sep. 2004, presently abandoned, which claims the benefit of U.S. Provisional Application No. 60/543,185, Kufbag, Restraint for Transporting Prisoners, filed 10 Feb. 2004 in accordance with 35 USC §§119 (e), 120 wherein the respective disclosures of which are hereby incorporated by reference herein.

FEDERALLY SPONSORED RESEARCH OR DEVELOPMENT

There has been no research or development sponsored in whole or part by the Federal government or any agency thereof in respect to the instant invention.

BACKGROUND OF INVENTION

1. Field of the Invention

The present invention specifically relates to a SOFT HAND RESTRAINT DEVICE FOR TRANSPORTING PRISONERS utilized to transport a prisoner in the custody of law enforcement authorities between various locations, as may be dictated by the individual circumstances. The soft hand restraint device for transporting prisoners provides a measure of safety for both the law enforcement personnel entrusted with the transport of the prisoner and the prisoner being transported. Law enforcement personnel are placed at reduced risk of attack and injury from the prisoner as the prisoner's hands are not available to use in a similar fashion as if handcuffs had been employed. The prisoner derives the benefit of having an increased obstacle in respect to impulsive episodes, which could result in the use of more severe means of physical restraint by law enforcement personnel. Further, the incidence of excess force to subdue an unruly prisoner during transport may be minimized, as the prisoner poses less dexterity to support a confrontation.

2. Description of the Related Art

An effective means for safely transporting prisoners has long been felt in the law enforcement community. The use of traditional handcuffs and plastic cuffs, wherein the prisoner's hands are afforded limited freedom of movement has lead to the loss of life of law enforcement personnel and prisoners due to altercations that ensued. In many instances the prisoner was able to grab the weapon of the law enforcement officer, wherein it was employed to assault the officer. There have also been instances wherein the wrist chains of shackles or handcuffs have been employed to choke the law enforcement officer charged with transporting the prisoner.

There have been numerous attempts made to overcome these issues as can be demonstrated by such inventions as U.S. Pat. No. 6,073,631, Safe Cross Cuffs to Wilhelmy, U.S. Pat. No. 5,551,086, Hand Restraint Device to Albanese, U.S. Pat. No. 4,469,096 Supplemental Hand Restraint Device to Rivadeneyra, and U.S. Pat. No. 5,031,641 Hand Restraint for Handcuffs by Upton. However, each of these examples still present various limitations that although reducing the threat level to law enforcement personnel charged with transporting prisoners, fail to eliminate the risk. In the case of Wilhelmy, the hands of the prisoner are exposed and are still free to grasp objects and personnel within the prisoners reach. Further, the principle means of incapacitating the prisoner is by extended wrist cuffs having a rigid insert wherein the cuffs are joined by a screwed connection, which maintains the geometry of the cross cuffs, and also presents a weapon for the prisoners use. In the event that the prisoner is able to overcome the transporting officer, the prisoner may use the cross cuffs to his advantage to choke the officer or crush his [officer's] extremities, as a function of the leverage provided by the cross cuffs. In regard to Albanese, the arrangement of the hand cuff about metal rings that enclose the wrists poses a similar risk as in Wilhelmy, except that the prisoner is provided a greater range of motion and can undertake a greater range of motion of an extremity upon which to perform an offensive act. It is also obvious that Albanese although countering the ability to utilize the hands individually to grasp, has outfitted the prisoner with a striking tool that may be employed with the hands in unison to chop, slap or punch with. Both Upton and Rivadeneyra present bags that may be disposed over a set of hand cuffs to prevent the prisoner from exercising his ability to grip, however both rely on the positioning of the bag by a strap or snap ring arrangement the passes over the hand cuff linkage. Given the bulk of the bag in contrast to the flexibility of the human hand and the prisoner's desire to free himself, the potential for freeing one or both hands is not improbable. Further the ability of the prisoner to grasp items is only limited by the denier of the fabric as the aspect of the mutual cooperation of the prisoner's hands is left unmitigated. The disadvantages posed by these attempts firmly evidence the need for a solution that will prevent a prisoner from using his hands in an offensive manner during transportation by law enforcement personnel. Further, although all of the aforementioned attempts at redressing the issue of restricting the prisoner from exercising the ability to utilize his hands in a manner that manifests an offensive posture provide a limited degree of success. These means fail to completely eliminate the threat. It would be most desirable to have a means at the beckon disposal of law enforcement personnel that would provide for the humane detention and transportation of prisoners wherein the prisoner's ability to utilize his hands in an offensive manner is negated.

Given the multitude of shortcomings and disadvantages regarding the existing approaches to securing prisoners' hands to ensure safety to all parties during their [prisoner's] transportation it would be desirable to have an affordable and convenient solution within the domain of the law enforcement community that is capable of securing the prisoner and reducing the threat to law enforcement personnel while equally minimizing the subjective elements of use and reduces aspects for a chance of escape. The present invention satisfies such a need.

SUMMARY OF THE INVENTION

The present invention specifically relates to a SOFT HAND RESTRAINT DEVICE FOR TRANSPORTING PRISONERS utilized to temporary debilitate a prisoner's capacity to exercise his hands in an offensive posture. This is accomplished by separably maintaining the hands in a thumb-to-thumb orientation within the plane of the front and rear side of the restraint whereby the middle and ring finger are splayed apart at a predetermined distance by a splay device, which interferes with the grip ergonomics, wherein the prisoner is unable to exert sufficient force to overcome the splay device and hence is unable to form a grip. The soft hand restraint device utilizes the fact that the hand requires the action of two groups of muscles to effect movement, intrinsic (those within the region of the hand) and extrinsic (those outside the region of the hand). The extrinsic muscles serve to properly align the joints and apply varying degrees of force through formation of a grip. The intrinsic muscles however, control the specific movements of the fingers (abduction and adduction) and allow the thumb to meet the finger tips (opposition). The intrinsic muscles are essential to establish fine manipulation, dexterity and grip stability. A developed hand is capable of an entire range of motions and is able to manipulate a variety of items of enormous diversity in size or shape. In order to be able to do this, the hand works in patterns of movement to form a variety of grips. The following are examples of grips that are commonly employed in daily living:

Power Grip—such as holding the handle of a broom or a hammer
Span Grip—using the tips of the fingers to grasp around an object such as a large dial
Pinch Grip—used in a variety of ways to hold small objects such as picking up a piece of pasta and writing
Lateral key pinch—used for holding and turning keys
Hook Grip—for carrying the shopping bags home
Spherical Grip—for throwing and catching balls[1]

[1] American Society for Surgery of the Hand, Essentials of Hand Surgery 2002

The splay device through interference with the alignment and cooperation of the various intrinsic and extrinsic muscles and the metacarpals and phalanges of the hand, prevent the formation of any of the above listed grips, which incapacitate the prisoner without inflicting any undue harm. The soft hand restraint may incorporate the splay device in its construction or in another embodiment, may utilize a reusable glove of disposable construction that may incorporate the splay device, where the gloved hands of the prisoner are subsequently placed in the soft hand restraint device.

The splay device through the abduction of the proximal phalanges of the middle finger and ring finger place the tendons and muscles of the middle finger (flexor pollicis longus, adductor pollicis (oblique and transverse head), flexor pollicis brevis, and opens pollicis) in conflict with the ring finger (flexor digitorum profundus 4 and 5, flexor digit minimi and abductor digiti minimi). This serves also to restrict the motion of the metacarpals of the index finger though the small finger in their respective travel over the trapezoid, capitate and hamate, thereby imposing a significant impediment for the prisoner in forming any of the aforementioned grips of any appreciable magnitude. In another embodiment, the proximal metacarpal of the thumb may be maintained in rigidly adducted compliance with the index finger proximal phalange, further restricting the motion about the trapezium thereby essentially locking all the metacarpals of the hand in a splayed configuration. This may be accomplished by a thumb adduction device incorporated into the soft hand restraint device or by way of a reusable glove of disposable construction that may incorporate a thumb adduction device, where the gloved hands of the prisoner are subsequently placed in the soft hand restraint device.

A first aspect of the soft hand restraint device for transporting prisoners may comprise:

a fabric pouch constructed of a lightweight washable durable rip-proof fabric material having a substantially rectangular shape of a predetermined size, having a first side, a second side, a first edge, a second edge, a top rear edge and a top front edge, wherein said fabric pouch is formed by folding the fabric so that the top rear edge is elevated to a predetermined height above the top front edge in a substantially parallel fashion, to accommodate the attachment of a wrist retaining strap, wherein the top rear edge has a cut-out of a predetermined width about its middle that substantially corresponds with the width of a handcuff retainer, wherein the top rear edge and top front edge are in matched agreement in a predetermined location such that adequate space is provided for the adequate accommodation of the linkage of a handcuff or shackle to be received; where they are joined by any means known in the Textile Arts to produce a seam satisfying the mechanical requirements of a physical restraint, further in the process of joining the top rear edge and top front edge, a front side and a rear side are formed that are of a substantially similar geometry, excepting those areas on the rear side set out to accommodate the attachment of wrist retaining straps, whereby the front side and rear side are joined at their respective first edge and second edge by any means known in the Textile Arts satisfying the mechanical requirements of a physical restraint, and having a partition seam that traverses from a midline of a base of fabric pouch; which is the point, wherein the demarcation of the front side and the rear side occurs; to a predetermined location in the proximity of the top rear edge and top front edge while simultaneously joining the front side and the rear side, wherein the partition seam terminates in a "T" shape and providing for adequate accommodation of the linkage of a handcuff or shackle to be received, thereby forming a septum within the soft hand restraint device that serves to separably secure the hands together by maintaining the hands in a thumb-to-thumb orientation within the plane of the front and rear side of the restraint whereby the middle and ring finger are splayed apart at a predetermined distance by a splay device, which interferes with the grip ergonomics, wherein the prisoner is unable to exert sufficient force to overcome the splay device and hence is unable to form a grip while simultaneously preventing the restrained individual from using his hands to grasp objects or individuals, wherein the area within the septum may be further configured by stitched splay seams in a predetermined shape to accommodate the pairing of the index and middle finger and the ring and small finger in pockets that splay these two pairs of fingers at a predetermined angle, which is tensionally maintained by a splay device, which comprises a means for maintaining a predetermined tension and splay angle, which may be selected from a group consisting of rigid polymeric wedges, chevron shaped metallic inserts, non-deformable plastic chevron shaped inserts and a combination thereof; which are permanently affixed in the fabric pouch such that the interior surface of the fabric pouch prevents direct contact with the hands of a prisoner, at least one retaining clip mechanism, comprising a spring latch closure having a male lead having at least one tensional element that is received in a corresponding female receptacle wherein, the male lead and the female receptacle further provide a means for the respective attachment of a male lead attachment strap and female receptacle attachment strap, which respectively comprise a material of construction having durability and strength commensurate with the demands of transporting prisoners, wherein the male lead is attached by the male lead attachment strap to the front side and is received in the female receptacle, which is attached by the female receptacle attachment strap to a handcuff retainer;

at least two wrist retaining straps, comprising a rectangular shaped flexible material of a predetermined size, having a first side, a second side, a top edge, a bottom edge, an attachment area, a wrist retaining strap hook fastener and a wrist retaining strap loop fastener, wherein the wrist retaining strap hook fastener has a predetermined shape and substantially similar dimensional characteristics of the wrist retaining strap first side to which it is affixed, and the wrist retaining strap loop fastener is of a predetermined shape and substantially similar dimensional characteristics of the wrist retaining strap second side to which it is affixed, wherein the wrist retaining straps are joined about the midsection of this construction in an area bordering the top edge and the bottom edge that may range to the width of the tabs formed in the fabric pouch top rear edge comprising an attachment area whereby the wrist retaining straps are joined in matched agreement with the tabs formed in the fabric pouch top rear edge by any means known in the Textile Arts;

a handcuff retainer which is joined to the soft hand restraint device rear side about the midline near the top rear edge by any means known in the Textile Arts, comprising a rectangular shaped flexible material of a predetermined size, having a first side, a second side, a top edge, a bottom edge, an attachment area, a handcuff retainer hook fastener and handcuff retainer loop fastener, wherein the handcuff retainer hook fastener is affixed to the handcuff retainer first side further comprises a predetermined shape and substantially similar dimensional characteristics of the handcuff retainer less the predetermined area of attachment area, which comprises an area about the midsection of the first side bordered by the top edge and the handcuff retainer hook fastener that ranges to the width of the handcuff retainer wherein the handcuff retainer is secured to the fabric pouch by any means known in the Textile Arts; the handcuff retainer loop fastener is located about the midline of the soft hand restraint front side so as to engage the handcuff retainer hook fastener when it is drawn over the fabric pouch top rear and front edges, the handcuff retainer second side is secured about the midsection to the female receptacle attachment strap whereby the retaining clip mechanism female receptacle is connected by any means known in the Textile Arts, a plurality of restraint grommets may comprise any waterproof, corrosion resistant grommet of a predetermined size having any construction known in the Textile Arts capable of penetrating heavy fabric with adequate flange width to resist pullout and compromise of the fabric while presenting a smooth rounded edge to any binding devices exposed to the grommet; being further capable of enduring the rigors anticipated in transporting prisoners; the restraint grommets are situated at predetermined locations about the fabric pouch in the general proximity of the fabric pouch top front edge and the handcuff retainer on the fabric pouch front side, wherein a corresponding restraint grommets are located on the fabric pouch rear side, a plurality of D-rings comprising any waterproof, corrosion resistant D-ring of a predetermined size having any construction known in the Textile Arts capable of being secured to heavy fabric with an adequate bearing surface width to resist pullout and compromise of the fabric while presenting a smooth rounded edges to any binding devices exposed to the D-ring; being further capable of enduring the rigors anticipated in transporting prisoners; the restraint D-rings are situated at predetermined locations about the fabric pouch in the general proximity of the fabric pouch top front edge, bottom edge, first side edge, second side edge and about the handcuff retainer on the fabric pouch front side, wherein a corresponding D-rings are located on the fabric pouch rear side, these provide for the attachment of shackles, waist chains and also provide for securing the fabric pouch about the prisoner's thighs to further restrict the use of his arms.

A second aspect of the soft hand restraint device for transporting prisoners may comprise a soft hand restraint device of similar construction to the first aspect further incorporating a thumb adduction device wherein the area within the septum may be further configured by stitched splay seams in a predetermined shape to accommodate the pairing of the thumb, index and middle finger and the ring and small finger in pockets that splay these two pairs of fingers at a predetermined angle, which is tensionally maintained by a splay device which comprises a means for maintaining a predetermined tension and splay angle which may be selected from a group consisting of rigid polymeric wedges, chevron shaped metallic inserts, non-deformable plastic chevron shaped inserts and a combination thereof; which are permanently affixed in the fabric pouch such that the interior surface of the fabric pouch prevents direct contact with the hands of a prisoner, and a thumb adduction device which comprises a means for maintaining the proximal metacarpal of the thumb may be maintained in rigidly adducted compliance with the index finger proximal phalange, wherein the means is selected from a group consisting of metal and non-deformable polymeric of predetermined shapes i.e. rings, clips, etc. that arrest the motion of the thumb which are permanently affixed in the fabric pouch such that the interior surface of the fabric pouch prevents direct contact with the hands of a prisoner.

A third aspect of the soft hand restraint device for transporting prisoners may comprise a soft hand restraint device of similar construction to the first aspect further incorporating a splay glove of similar construction as may be gleaned from U.S. Pat. No. 7,210,172B1, Fingertip Flexor Glove to Adams, Jr. or U.S. Pat. No. 5,604,933, Hand and Wrist Restraint for a Patient to Stephens, where the splay glove is arranged to accommodate the pairing of the thumb, index and middle finger and the ring and small finger in pockets that splay these two pairs of fingers at a predetermined angle, which is tensionally maintained by a splay device which comprises a means for maintaining a predetermined tension and splay angle, which may be selected from a group consisting of rigid polymeric wedges, chevron shaped metallic inserts, non-deformable plastic chevron shaped inserts and a combination thereof; which are permanently affixed to the splay glove. Further the outer surface of the splay glove would have a predetermined area covered by hook-loop fasteners which would be engaged by corresponding fasteners within the soft hand restraint device and would affix the glove. This would also provide an audible notice to transporting law enforcement personnel that the prisoner had freed himself from the soft hand restraint device, such that an appropriate response could be initiated. In another embodiment a thumb adduction glove device having a predetermined shape may be comprised of metal or plastic construction that could be incorporated into the structure of the splay glove to form a thumb adduction splay glove.

BRIEF DESCRIPTION OF THE DRAWINGS

FIG. 1A is a drawing of a cut-away perspective view of the SOFT HAND RESTRAINT DEVICE FOR TRANSPORTING PRISONERS, engaged over the handcuffed hands of an individual prisoner, wherein the index and middle fingers, and ring and small finger are respectively paired and these pairs are maintained in splayed position by way of stitched splay seams in conjunction with a splay device, which is shown in DETAIL A, a cross-sectional view to FIG. 2A is denoted, in accordance with the present invention.

FIG. 1B is a drawing of a cut-away perspective view of the SOFT HAND RESTRAINT DEVICE FOR TRANSPORTING PRISONERS, engaged over the handcuffed hands of an individual prisoner, wherein the thumb, index and middle fingers, and ring and small finger are respectively paired and these pairs are maintained in splayed position by way of stitched splay seams in conjunction with a splay device and a thumb adduction device, which is shown in DETAIL B, a cross-sectional view to FIG. 2B is denoted, in accordance with the present invention.

FIG. 1C is a drawing of a cut-away perspective view of the SOFT HAND RESTRAINT DEVICE FOR TRANSPORTING PRISONERS, engaged over the handcuffed hands of an individual prisoner, wherein the left hand is fitted with an adduction-splay glove and the right hand is fitted with a splay glove, both of which are enclosed in a fabric pouch wherein hook-loop fasteners on the gloves are engaged by corresponding hook-loop fasteners on the fabric pouch second side and are maintained in adducted/splayed position by way of stitched splay seams in conjunction with the use of a splaying and thumb adduction device, in accordance with the present invention.

FIG. 2A is a drawing of a side cross-sectional view of the SOFT HAND RESTRAINT DEVICE FOR TRANSPORTING PRISONERS referred to in FIG. 1A, wherein the breadth of the orientation, dimensional aspects and inter-relationship of the components with a splayed hand of a prisoner may be gleaned, in accordance with the present invention.

FIG. 2B is a drawing of a side cross-sectional view of the SOFT HAND RESTRAINT DEVICE FOR TRANSPORTING PRISONERS referred to in FIG. 1B, wherein the breadth of the orientation, dimensional aspects and inter-relationship of the components with the adducted and splayed hand of a prisoner may be gleaned, in accordance with the present invention.

FIG. 3A is a drawing of a front view of the SOFT HAND RESTRAINT DEVICE FOR TRANSPORTING PRISONERS wherein the hands of a prisoner are fitted with splay gloves, which are enclosed in the fabric pouch wherein hook-loop fasteners on the gloves are engaged by corresponding hook-loop fasteners on the fabric pouch second side and are maintained in splayed position by way of stitched splay seams in conjunction with the use of a splay device, in accordance with the present invention.

FIG. 3B is a drawing of a front view of the SOFT HAND RESTRAINT DEVICE FOR TRANSPORTING PRISONERS wherein the hands of a prisoner are fitted with a thumb adduction splay gloves, which are enclosed in a fabric pouch wherein hook-loop fasteners on the gloves are engaged by corresponding hook-loop fasteners on the fabric pouch second side and are maintained in adducted/splayed position by way of stitched splay seams in conjunction with the use of a splaying and thumb adduction device, in accordance with the present invention.

FIG. 3C is a drawing of a back view of the SOFT HAND RESTRAINT DEVICE FOR TRANSPORTING PRISONERS wherein the areas of the stitched splay seams for retaining the hands of a prisoner in a splayed position are shown in relationship to the various appurtenances as D-rings and restraint, in accordance with the present invention.

FIG. 4 is a drawing of a bottom view of the handcuff retainer, showing the location of hook-loop closures attached which correspond with complimentary fasteners located on the SOFT HAND RESTRAINT DEVICE FOR TRANSPORTING PRISONERS, in accordance with the present invention.

FIG. 5 is a drawing of a front view of the wrist retaining strap, showing the location of hook-loop closures attached which correspond with complimentary fasteners located on the adjacent end of the opposite side and delineate the area where these are secured to the SOFT HAND RESTRAINT DEVICE FOR TRANSPORTING PRISONERS, in accordance with the present invention.

DETAILED DESCRIPTION OF THE PRESENTLY PREFERRED EMBODIMENTS

Figure 6A:
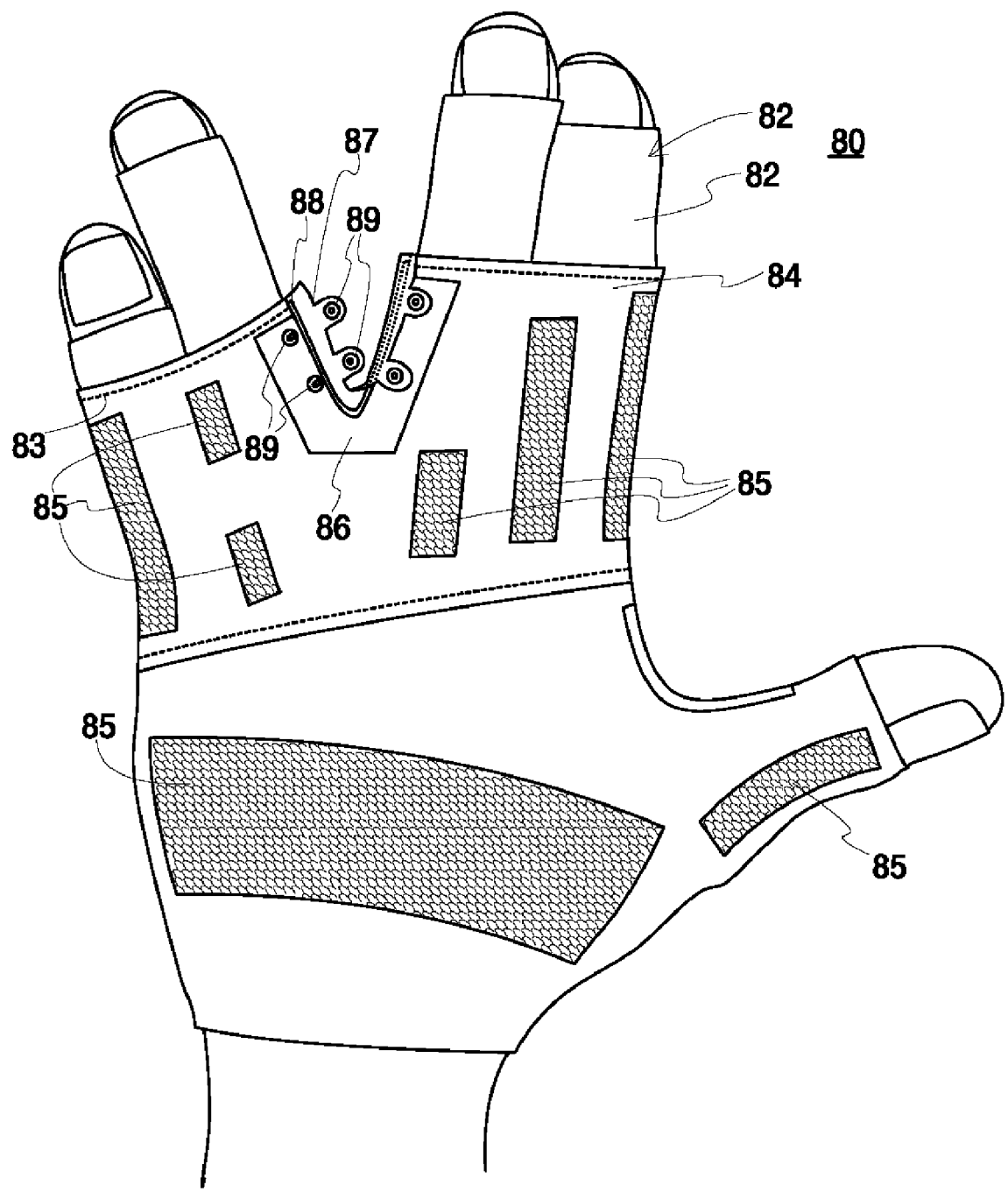
FIG. 6A is a drawing of a top view of a splay glove that may be utilized in conjunction with the SOFT HAND RESTRAINT DEVICE FOR TRANSPORTING PRISONERS, in accordance with the present invention.

FIGS. 1A-6B illustrate an embodiment of an SOFT HAND RESTRAINT DEVICE FOR TRANSPORTING PRISONERS in accordance with the present invention.

Referring to FIGS. 1A-1C, the present embodiment of the SOFT HAND RESTRAINT DEVICE FOR TRANSPORTING PRISONERS is generally shown at 100. The SOFT HAND RESTRAINT DEVICE FOR TRANSPORTING PRISONERS, 100 may comprise a fabric pouch 10, a retaining clip mechanism 20, a wrist retaining strap 30, restraint grommets 40, a handcuff retainer 50, a splay device 70, stitched splay seams 74 and a plurality of D-rings 102.

Referring again to FIGS. 1A-1C, the fabric pouch 10 may comprise any lightweight washable durable rip-proof material known in the Textile Arts capable of satisfying the mechanical demands and environmental rigors of serving as a physical restraint i.e. nylon, polypropylene, canvas duck, polyester, washable leather and reinforced vinyl, having a generally rectangular shape of a predetermined size, having a first side 11 and second side 12 (FIGS. 2A, 2B), a first edge 13, a second edge 14, a top rear edge 16 (FIGS. 2A, 2B) and a top front edge 18. In another embodiment the fabric pouch 10 may incorporate foam padding between the first side 11 and the second side 12. Wherein the fabric pouch 10 may be formed by folding the fabric so that the top rear edge 16 (FIGS. 2A, 2B) is elevated to a predetermined height above the top front edge 18 in a substantially parallel fashion, so as to accommodate the attachment of a wrist retaining strap 30 (FIGS. 2A, 2B, 3A, 3B, 5). Further the top rear edge 16 (FIGS. 2A, 2B) may have a cut-out of a predetermined width about its middle that substantially corresponds with the width of the handcuff retainer 50 (FIGS. 3A, 3B, 5), wherein the top rear edge 16 (FIGS. 2A, 2B) and top front edge 18 are in matched agreement where they are joined by any means known in the Textile Arts such as stitching, gluing, fusing, riveting or weaving to produce a seam satisfying the mechanical requirements of a physical restraint, in a predetermined location such that adequate space is provided for the adequate accommodation of the linkage of a handcuff or shackle to be received. In the process of joining the top rear edge 16 (FIGS. 2A, 2B) and top front edge 18, a front side 15 and a rear side 17 (FIGS. 2A, 2B) are formed that are of a substantially similar geometry, excepting those areas on the rear side 17 (FIGS. 2A, 2B) set out to accommodate the attachment of the wrist retaining straps 30 (FIGS. 2A, 2B, 3A, 3B, 5). The front side 15 and rear side 17 are joined at their respective first edge 13 and second edge 14 by any means known in the Textile Arts such as stitching, gluing, fusing, riveting or weaving to produce a seam satisfying the mechanical requirements of a physical restraint. From a base of the midline fabric pouch 10, which is the point, wherein the demarcation of the front side 15 and the rear side 17 (FIGS. 2A, 2B) occurs; a partition seam 19, which joins the front side 15 and the rear side 17 (FIGS. 2A, 2B) to previously indicated standards, traverses from the base of the pouch 10 to a predetermined location in the proximity of the top rear edge 16 (FIGS. 2A, 2B) and top front edge 18, wherein the partition seam 19 terminates in a "T" shape and providing for adequate accommodation of the linkage of a handcuff or shackle to be received. The partition seam 19 forms a septum within the soft hand restraint device 100, which serves to secure the hands together, while simultaneously preventing the restrained individual from using his hands to grasp objects or individuals. In another embodiment, the fabric pouch 10 may be constructed of a double layer of fabric that may be bonded or stitched to itself to increase the fabric's strength. The area within the septum may be further configured by stitched splaying seams 74 in a predetermined shape to accommodate the pairing of the index and middle finger and the ring and small finger in pockets that splay these two pairs of fingers at a predetermined angle, which is tensionally maintained by a splay device 70 that is affixed in the proximal location of the splayed finger pockets such that splayed fingers are tensionally maintained in the desired position. In another embodiment the area within the septum may be further configured by stitched splaying seams 74 in a predetermined shape to accommodate the pairing of the thumb, index and middle finger and the ring and small finger in pockets that splay these two pairs of fingers at a predetermined angle, which is tensionally maintained by a splay device 70 that is affixed in the proximal location of the splayed finger pockets such that splayed fingers are tensionally maintained in the desired position and a thumb adduction device 92 (FIG. 1B DETAIL B) which comprises a means for maintaining the proximal metacarpal of the thumb in rigidly adducted compliance with the index finger proximal phalange, wherein the means is selected from a group consisting of metal and non-deformable polymeric construction of predetermined shapes i.e. rings, clips, etc. that arrest the motion of the thumb which are permanently affixed in the fabric pouch 10 by any means accepted in the Textile Arts suitable for severe service and repeated laundering; such that the fabric pouch second side (interior surface) 12 (FIG. 2B) prevents direct contact with the hands of a prisoner. The soft hand restraint device 100 further may comprise a plurality of D-rings 102 that are attached by any means known in the Textile Arts capable of withstanding the rigors of prisoner transport, at predetermined locations about the fabric pouch first edge 13, second edge 14, bottom edge 15, first side 11 and rear side 17 to facilitate the attachment of additional restraint devices and apparel as deemed appropriate i.e. shackles, waist restraint belts, etc. Additionally the D-rings 102 permit the soft hand restraint device 100 to be secured to other structures, chairs, personnel or the prisoner's hands may be bound to his thighs as needs dictate.

The retaining clip mechanism 20 is designed to provide a convenient means for providing a secondary fastener to secure the soft hand restraint device 100 in place. The retaining clip mechanism 20 may comprise a spring latch closure having a male lead 22 having at least one tensional element that is received in a corresponding female receptacle 24. The retaining clip mechanism 20 may further comprise any clip mechanism known in the Mechanical Arts that may satisfy the requirements for a fastener that will endure the rigors anticipated in transporting prisoners, which may be readily engaged and disengaged. Both the male lead 22 and the female receptacle 24 may further provide a means for the respective attachment of a male lead attachment strap 21 and female receptacle attachment strap 26. The male lead attachment strap 21 and female receptacle attachment strap 26 may comprise a material of construction having durability and strength commensurate with the demands of transporting prisoners, wherein materials such as leather, plastic, fabric or a combination thereof may be considered. In another embodiment the male lead attachment strap 21 and female receptacle attachment strap 26 may be made adjustable by incorporating a buckle or cinching means i.e. a plurality of D-rings 102, friction catches, etc. In another embodiment, the retaining clip mechanism 20 may incorporate construction that may be gleaned from U.S. Pat. No. 4,100,657 to Minolla or U.S. Pat. No. 4,468,843 to Duclos, et al.

The wrist retaining strap 30 may comprise a rectangular shaped flexible material of a predetermined size, having a first side 31 (FIG. 5), a second side 32, (FIG. 5) a top edge 33 (FIG. 5), a bottom edge 34 (FIG. 5), an attachment area 35 (FIG. 5), a wrist retaining strap hook fastener 37 (FIG. 5) and a wrist retaining strap loop fastener 38 (FIG. 5). The wrist retaining strap 30 may have the wrist retaining strap hook fastener 37 (FIG. 5) of a predetermined shape and substantially similar dimensional characteristics affixed to the first side 31 (FIG. 5); and a wrist retaining strap loop fastener 38 (FIG. 5) of a predetermined shape and substantially similar dimensional characteristics affixed to the second side 32 (FIG. 5). The wrist retaining straps 30 (FIGS. 2A, 2B, 3A, 3B, 3C) may be joined in matched agreement with the tabs formed in the top rear edge 16 (FIGS. 2, 3) by any means known in the Textile Arts such as stitching, gluing, fusing, riveting or weaving to produce a bond satisfying the mechanical requirements of a physical restraint. In another embodiment the wrist retaining strap 30 may reverse the location of the wrist retaining strap hook fastener 37 (FIG. 5) and wrist retaining strap loop fastener 38 (FIG. 5).

The restraint grommets 40 (FIGS. 2A, 2B, 3A, 3B) may comprise any waterproof, corrosion resistant grommet of a predetermined size having any construction known in the Textile Arts capable of penetrating heavy fabric with adequate flange width to resist pullout and compromise of the fabric while presenting a smooth rounded edge to any binding devices exposed to the grommet, further capable of enduring the rigors anticipated in transporting prisoners. The restraint grommet 40 is situated at a predetermined location about the fabric pouch 10 in the general proximity of the top front edge 18 (FIGS. 2A, 2B) and the handcuff retainer 50 (FIGS. 2A, 2B, 3A, 3B) on the front side 15 (FIGS. 2A, 2B), wherein corresponding restraint grommets 40 (FIGS. 2A, 2B) are located on the rear side 17 (FIGS. 2A, 2B).

The handcuff retainer 50 may comprise a rectangular shaped flexible material of similar construction as the fabric pouch 10 (FIGS. 1A-1C) of a predetermined size, having a first side 51, a second side 52, a top edge 53, a bottom edge 54, an attachment area 56, a handcuff retainer hook fastener 57 and handcuff retainer loop fastener 58 (FIG. 1). The handcuff retainer 50 may be joined to the soft hand restraint device rear side 17 about the midline near the top rear edge 16 (FIGS. 2, 3) by any means known in the Textile Arts such as stitching, gluing, fusing, riveting or weaving to produce a bond satisfying the mechanical requirements of a physical restraint.

Referring to FIG. 1A (DETAIL A) the splay device is generally shown at 70. The splay device 70 may comprise a means for tensionally splaying the prisoner's hands by abduction of the ring and middle finger, which are respectively paired with the small and index fingers at a predetermined angle wherein the splay device 70 effectively prevents the formation of a grip by the prisoner. The splay device 70 may have a splay device body 72 having a predetermined shape and size designed to form an optimum splaying angle, which may be constructed of a polymeric material demonstrating adequate compressive strength to resist compressive forces which would collapse the splay device 70. The splay device 70 may further comprise a reinforcement splay 73 that may be either attached to or incorporated in the splay device body 72. The splay device 72 is designed to be permanently affixed into the body of the fabric pouch 10 such that it is contained between the fabric pouch first side 11 and the fabric pouch second side 12 (FIGS. 2A, 2B), to prevent contact with the prisoner. The splay device 70 is designed to withstand the rigors of routine laundering of the soft hand restraint device 100, without compromising its compressive strength or significant change of its morphology. In another embodiment, the splay device 70 may comprise means for maintaining a predetermined tension and splay angle, which may be selected from a group consisting of rigid polymeric wedges, chevron shaped metallic inserts, non-deformable plastic chevron shaped inserts, wooden wedges and a combination thereof; which are adequately padded and permanently affixed in the fabric pouch 10 such that the fabric pouch second side (interior surface) 12 (FIG. 2A, 2B) prevents direct contact with the hands of a prisoner.

Referring to FIG. 1B (DETAIL B) the thumb adduction device is generally shown at 92. The thumb adduction device 92 may comprise a means for tensionally adducting the prisoner's hands by maintaining the proximal metacarpal of the thumb in rigidly adducted compliance with the index finger proximal phalange wherein the splay device 70 effectively prevents the formation of a grip by the prisoner. The thumb adduction device 92 may have a predetermined shape and size designed to form a retaining saddle, which may be constructed from a material of construction selected from a group consisting of structural polymeric materials, metals, fiberglass or combinations thereof demonstrating adequate tensile and compressive strength to resist destructive forces which would collapse or fracture the thumb adduction device 92. The thumb adduction device 92 is designed to be permanently affixed into the body of the fabric pouch 10 such that it is contained between the fabric pouch first side 11 and the fabric pouch second side 12 (FIG. 2B), to prevent contact with the prisoner. The thumb adduction device 92 is designed to withstand the rigors of routine laundering of the soft hand restraint device 100, without compromising its compressive strength or significant change of its morphology.

Referring to FIG. 1C, a cut-away perspective view of the soft hand restraint device is generally shown at 100 wherein the soft hand restraint device is utilized in conjunction with a splay glove 80 and a thumb adduction-splay glove 90. The soft hand restraint device 100 may further comprise a splay glove 80 of similar construction as may be gleaned from U.S. Pat. No. 7,210,172B1, Fingertip Flexor Glove to Adams, Jr. or U.S. Pat. No. 5,604,933, Hand and Wrist Restraint for a Patient to Stephens, where the splay glove 80 is arranged to accommodate the pairing of the thumb, index and middle finger and the ring and small finger in pockets that splay these two pairs of fingers at a predetermined angle, which is tensionally maintained by a splay stay 88 (FIGS. 6A, 6B) which comprises a means for maintaining a predetermined tension and splay angle, which may be selected from a group consisting of rigid polymeric wedges, chevron shaped metallic inserts, non-deformable plastic chevron shaped inserts and a combination thereof; which may be detachably or permanently affixed to the splay glove 80 by a splay stay retainer 86. Further the outer surface of the splay glove 80 would have a predetermined area covered by hook-loop fasteners 85, which would be engaged by corresponding fasteners within the soft hand restraint device 100 (FIGS. 2A, 2B) and would affix the splay glove 80. This arrangement would also provide an audible notice to transporting law enforcement personnel that the prisoner had freed himself from the soft restraint device 100 or was attempting to do so, such that an appropriate response could be initiated. In another embodiment, a thumb adduction glove device 94 having a predetermined shape comprised of metal or plastic construction which may be detachably or permanently affixed to the splay glove 80 by a thumb adduction stay retainer 96 to form a thumb adduction splay glove 90. Both embodiments of the splay glove 80 and thumb adduction splay glove 90 are designed to be received by the fabric pouch 10 where they are in positional agreement with the area within the septum configured by the stitched splaying seams 74 to accommodate the pairing of the index and middle finger and the ring and small finger in pockets, or thumb, index and middle finger and the ring and small finger in pockets that splay these two pairs of fingers at a predetermined angle and are further maintained by the splay device 70.

Referring to FIGS. 2A-2B, a cut-away sectional view of the soft hand restraint device is in the process of restraining an individual is generally shown at 100. The soft hand restraint device 100 is analogous to a strait jacket for the hands wherein the hands of a prisoner are retained in a confined space formed by the soft hand restraint device second side 12 bounded by a septum formed by the partition seam 19 and the second edge 14 (FIGS. 1A, 1B, 1C) in the example or the first edge 13. The prisoner's hands are further secured by the soft hand restraint device 100 through the use of the wrist retaining straps 30 which encircle the wrists of the prisoner and plastic ties that are routed through the restraint grommets 40 located in a somewhat superior proximity to the handcuffs, which also serve to securely maintain the soft hand restraint device 100 in position over the prisoner's hands. In cases where the soft hand restraint device 100 is used in conjunction with handcuffs the handcuff retainer 50 serves traverses the handcuff linkage wherein the handcuff retainer hook fastener 57 FIG. 4) engages the handcuff retainer loop fastener 58 (FIGS. 1A, 1B, 1C) and is additionally secured by engaging the male lead 22 and the female receptacle 24 of the retaining clip mechanism 20. FIG. 2A reflects the typical orientation of the prisoner's hand in the septum of the soft hand restraint device 100 when splayed as a function of the stitched splaying seams 74 (FIGS. 1A, 1B, 1C) or the splay glove 80 (FIG. 6A), where the positional relationship to the hook-loop fastener 85 which corresponds to the hook-loop fasteners 85 (FIG. 3A) located on the stay glove 80 (FIG. 3A). FIG. 2B reflects the typical orientation of the prisoner's hand in the septum of the soft hand restraint device 100 when the thumb is adducted and the paired fingers splayed as a function of the stitched splaying seams 74 (FIGS. 1A, 1B, 1C) or the thumb adduction splay glove 90 (FIG. 6B), where the positional relationship to the hook-loop fastener 85 which corresponds to the hook-loop fasteners 85 (FIG. 3B) located on the thumb adduction stay glove 80 (FIG. 3B). The soft hand restraint device 100 may be secured in front of or behind the back of the prisoner as dictated by the safety concerns of the transporting law enforcement personnel.

Referring to FIGS. 3A-3B, the soft hand restraint device is generally shown at 100, wherein the retaining clip mechanism 20 is shown in the closed position wherein the male lead 22, which is attached by the male lead attachment strap 21 to the front side 15; is received in the female receptacle 24 which is attached by the female receptacle attachment strap 26 to the handcuff retainer 50. In another embodiment, the male lead 22 may be attached by the male lead attachment strap 21 to the handcuff retainer 50 and the female receptacle attachment strap 26 to the front side 15. FIG. 3A reflects the typical orientation of the prisoner's hand in the septum of the soft hand restraint device 100 when splayed as a function of the splay device 70, stitched splaying seams 74 (FIGS. 1A, 1B, 1C) or when utilized with the splay glove 80 (FIG. 6A), where the positional relationship to the hook-loop fastener 85 which corresponds to the hook-loop fasteners 85 (FIG. 2A) located on the stay glove 80. FIG. 3B reflects the typical orientation of the prisoner's hand in the septum of the soft hand restraint device 100 when the thumb is adducted and the paired fingers splayed as a function of the splay device 70, the stitched splaying seams 74 (FIGS. 1A, 1B, 1C) or utilized in conjunction with the thumb adduction splay glove 90 (FIG. 6B), where the positional relationship to the hook-loop fastener 85 which corresponds to the hook-loop fasteners 85 (FIG. 2B) located on the thumb adduction stay glove 90.

Referring to FIG. 3C, the back side of the soft hand restraint device is generally shown at 100, wherein the stitched splay seam 74 and the splay device 70 incorporated into the fabric pouch 10 (FIG. 1A) are shown in relationship to the restraint grommets 40, and D-rings 102. In another embodiment, the stitched splay seam 74 may have the thumbs adducted and further utilize the thumb adduction device 92 (FIG. 1B) to maintain the thumbs in an adducted position within the fabric pouch 10 (FIG. 1B). The various positions of the D-rings 102 permit webbing and additional restraint devices to be connected to the soft hand restraint device 100 to provide an additional measure of security or convenience for the transporting law enforcement personnel.

Referring to FIG. 4, the handcuff retainer is generally shown at 50. The handcuff retainer 50 may comprise a rectangular shaped flexible material of a similar construction as the fabric pouch 10 (FIGS. 1A-1C) of predetermined size, having a first side 51, a second side 52, a top edge 53, a bottom edge 54, an attachment area 56, a handcuff retainer hook fastener 57 and handcuff retainer loop fastener 58 (FIGS. 1A, 1B, 1C). The handcuff retainer 50 may have the handcuff retainer hook fastener 57 of a predetermined shape and substantially similar dimensional characteristics less the predetermined area of attachment area 56 affixed to the first side 51. The handcuff retainer 50 may be attached to an element of the retaining clip mechanism 20, in the present embodiment the handcuff retainer second side 52 may have secured about the midsection of the female receptacle attachment strap 26 whereby the retaining clip mechanism female receptacle 24 is connected. In another embodiment, the handcuff retainer second side 52 may have secured about the midsection the male lead attachment strap 21 whereby the retaining clip mechanism male lead 22 is connected. The attachment area 56 comprises an area about the midsection of the first side 51 bordered by the top edge 53 and the handcuff retainer hook fastener 57 that may range to the width of the handcuff retainer 50. The handcuff retainer loop fastener 58 (FIGS. 1A, 1B, 1C) is located about the midline of the soft hand restraint front side 15 so as to engage the handcuff retainer hook fastener 57 when it is drawn over the top rear and front edges 16, 18 (FIGS. 1A, 1B, 1C, 2A, 2B) respectively. The handcuff retainer 50 may be joined to the soft hand restraint device rear side 17 about the midline near the top rear edge 16 (FIGS. 2A, 2B, 3A, 3B) by any means known in the Textile Arts such as stitching, gluing, fusing, riveting or weaving to produce a bond satisfying the mechanical requirements of a physical restraint. In another embodiment the handcuff retainer 50 may reverse the location of the handcuff retainer hook fastener 57 and handcuff retainer loop fastener 58 (FIGS. 1A, 1B, 1C). The handcuff retainer hook fastener 57 and handcuff retainer loop fastener 58 (FIGS. 1A, 1B, 1C) also serve to alert transporting law enforcement personnel of an escape attempt due to the distinctive noise upon the disengagement of the hook and loop fasteners.

Referring to FIG. 5, the wrist retaining strap is generally shown at 30. The wrist retaining strap 30 may comprise a rectangular shaped flexible material of a predetermined size, having a first side 31, a second side 32, a top edge 33, a bottom edge 34, an attachment area 35, a wrist retaining strap hook fastener 37 and a wrist retaining strap loop fastener 38. The wrist retaining strap 30 may have the wrist retaining strap hook fastener 37 of a predetermined shape and substantially similar dimensional characteristics affixed to the first side 31; and a wrist retaining strap loop fastener 38 of a predetermined shape and substantially similar dimensional characteristics affixed to the second side 32. About the midsection of this construction an area bordering the top edge 33 and the bottom edge 34 that may range to the width of the tabs formed in the top rear edge 16 (FIGS. 2A, 2B) comprises the attachment area 35. The wrist retaining straps 30 (FIGS. 2A, 2B, 3A, 3B, 3C) may be joined in matched agreement with the tabs formed in the top rear edge 16 (FIGS. 2A, 2B, 3A, 3B) by any means known in the Textile Arts such as stitching, gluing, fusing, riveting or weaving to produce a bond satisfying the mechanical requirements of a physical restraint. In another embodiment the wrist retaining strap 30 may reverse the location of the wrist retaining strap hook fastener 37 and wrist retaining strap loop fastener 38.

Referring to FIG. 6A the splay glove is generally shown at 80. The splay glove 80 may comprise a body 82 having the general shape of a hand and finger which may be open at the fingertips, which is covered about the area of the metacarpals and distal phalanges by a reinforced band 84 that is affixed by glove stitching 83 and incorporates a splay stay retainer 86, which maintains a splay stay 88 in a desired position by a splay stay retainer flap 87 incorporating tabs with closures 89 that are received by corresponding closures 89 on the stay retainer 86. The splay glove 80 may be constructed of any material known in the Textile Arts suitable for the manufacture of a restraint glove and having ability to be laundered without significant compromise of strength or shrinkage. The reinforced band 84 may also be adhered to the glove body 82 by gluing, thermoforming, riveting, interweaving or any other suitable means known in the Textile Arts. The reinforced band 84 may comprise a material of construction selected from a group consisting of leather, woven fiberglass, high strength polymers, duck, sailcloth, metallic meshes and combinations thereof. The splay glove 80 may further comprise similar construction as may be gleaned from U.S. Pat. No. 7,210, 172B1, Fingertip Flexor Glove to Adams, Jr. or U.S. Pat. No. 5,604,933, Hand and Wrist Restraint for a Patient to Stephens, where the splay glove 80 is arranged to accommodate the pairing of the index and middle finger and the ring and small finger in pockets that splay these two pairs of fingers at a predetermined angle, which is tensionally maintained by a splay stay 88 which comprises a means for maintaining a predetermined tension and splay angle, which may be selected from a group consisting of rigid polymeric wedges, chevron shaped metallic inserts, non-deformable plastic chevron shaped inserts and a combination thereof; which may be detachably or permanently affixed to the splay glove 80 by a splay stay retainer 86. Further the outer surface of the splay glove 80 would have a predetermined area covered by hook-loop fasteners 85, which would be engaged by corresponding fasteners within the soft hand restraint device 100 (FIG. 2A) and would affix the splay glove 80. This arrangement would also provide an audible notice to transporting law enforcement personnel that the prisoner had freed himself from the soft restraint device 100 or was attempting to do so, such that an appropriate response could be initiated. In another embodiment, a thumb adduction glove device 94 having a predetermined shape comprised of metal or plastic construction which may be detachably or permanently affixed to the splay glove 80 by a thumb adduction stay retainer 96 to form a thumb adduction splay glove 90. The splay glove 80 is designed to be received by the fabric pouch 10 (FIG. 1A) where it is maintained in positional agreement with the area of the septum configured by the stitched splaying seams 74 to accommodate the pairing of the index and middle finger and the ring and small finger in pockets that splay these two pairs of fingers at a predetermined angle and are further maintained by the splay device 70 (FIG. 1A).

Figure 6B:
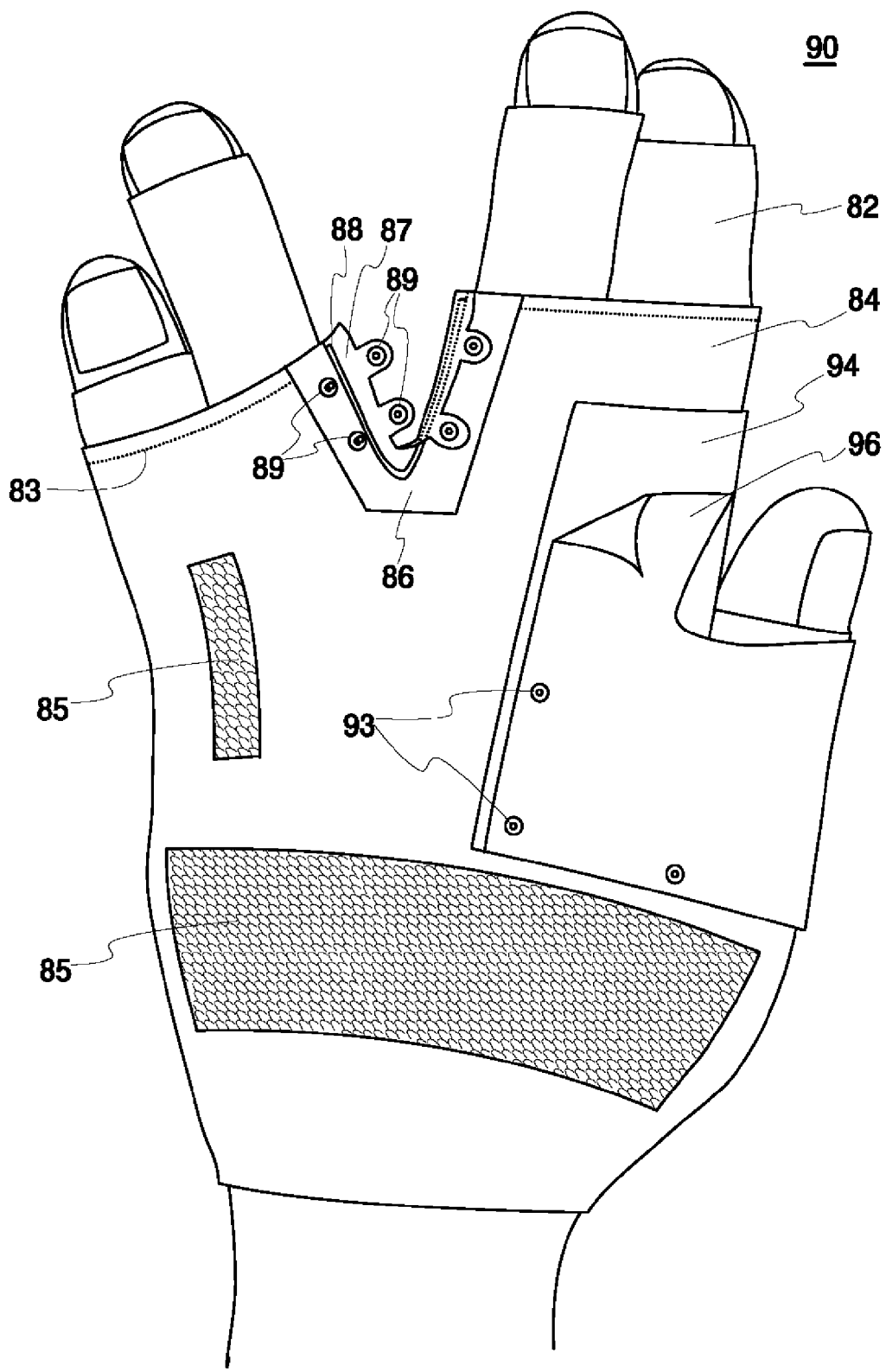
FIG. 6B is a drawing of a top view of a thumb adduction splay glove that may be utilized in conjunction with the SOFT HAND RESTRAINT DEVICE FOR TRANSPORTING PRISONERS, in accordance with the present invention.

Referring to FIG. 6B the thumb adduction splay glove is generally shown at 90. The thumb adduction splay glove 90 may comprise a body 82 having the general shape of a hand and finger which may be open at the fingertips, which is covered about the area of the metacarpals and distal phalanges by a reinforced band 84 that is affixed by glove stitching 83 and incorporates a splay stay retainer 86, which maintains a splay stay 88 in a desired position by a splay stay retainer flap 87 incorporating tabs with closures 89 that are received by corresponding closures 89 on the stay retainer 86, a thumb adduction glove device 94 comprises a means for tensionally adducting the prisoner's hands by maintaining the proximal metacarpal of the thumb in rigidly adducted compliance with the index finger proximal phalange; having a predetermined shape comprised of metal or plastic construction which may be detachably or permanently affixed to the reinforced band 84 by a thumb adduction retainer 96 which is affixed by closures 93 that are received by corresponding closures 93 on the reinforced band 84. The thumb adduction glove device The thumb adduction splay glove 90 may be constructed of any material known in the Textile Arts suitable for the manufacture of a restraint glove and having ability to be laundered without significant compromise of strength or shrinkage. The reinforced band 84 may also be adhered to the glove body 82 by gluing, thermoforming, riveting, interweaving or any other suitable means known in the Textile Arts. The reinforced band 84 may comprise a material of construction selected from a group consisting of leather, woven fiberglass, high strength polymers, duck, sailcloth, metallic meshes and combinations thereof. The thumb adduction splay glove 90 may further comprise similar construction as may be gleaned from U.S. Pat. No. 7,210,172B1, Fingertip Flexor Glove to Adams, Jr. or U.S. Pat. No. 5,604,933, Hand and Wrist Restraint for a Patient to Stephens, where the thumb adduction splay glove 90 is arranged to accommodate the pairing of the thumb, index and middle finger and the ring and small finger in pockets that splay these two pairs of fingers at a predetermined angle, which is tensionally maintained by a splay stay 88 which comprises a means for maintaining a predetermined tension and splay angle, which may be selected from a group consisting of rigid polymeric wedges, chevron shaped metallic inserts, non-deformable plastic chevron shaped inserts and a combination thereof; which may be detachably or permanently affixed to the thumb adduction splay glove 90 by a splay stay retainer 86. Further the outer surface of the thumb adduction splay glove 90 would have a predetermined area covered by hook-loop fasteners 85, which would be engaged by corresponding fasteners within the soft hand restraint device 100 (FIG. 2B) and would affix the thumb adduction splay glove 90. This arrangement would also provide an audible notice to transporting law enforcement personnel that the prisoner had freed himself from the soft restraint device 100 or was attempting to do so, such that an appropriate response could be initiated. In another embodiment, a thumb adduction glove device 94 having a predetermined shape comprised of metal or plastic construction which may be detachably or permanently affixed to the splay glove 80 by a thumb adduction stay retainer 96 to form a thumb adduction splay glove 90. The thumb adduction splay glove 90 is designed to be received by the fabric pouch 10 (FIG. 1B) where it is maintained in positional agreement with the area of the septum configured by the stitched splaying seams 74 to accommodate the pairing of the thumb, index and middle finger and the ring and small finger in pockets that splay these two pairs of fingers at a predetermined angle and are further maintained by the splay device 70 (FIG. 1B) and the thumb adduction device 92 (FIG. 1B).

While the embodiments of the present invention disclosed herein are presently considered to be preferred, various changes and modifications can be made without departing from the spirit and scope of the present invention. The scope of the present invention is indicated in the appended claims, and all changes that come within the meaning and range of equivalents are intended to be embraced therein.

What is claimed is:

1. A soft hand restraint device for transporting prisoners comprising:
    a fabric pouch constructed of a lightweight washable durable rip-proof fabric material having a substantially rectangular shape of a predetermined size, having a first side, a second side, a first edge, a second edge, a top rear edge and a top front edge, wherein said fabric pouch is formed by folding the fabric so that the top rear edge is elevated to a predetermined height above the top front edge in a substantially parallel fashion, to accommodate the attachment of a wrist retaining strap, further wherein the top rear edge has a cut-out of a predetermined width about its middle that substantially corresponds with the width of a handcuff retainer, wherein the top rear edge and top front edge of the cut-out are in matched agreement in a predetermined location such that adequate space is provided for the adequate accommodation of the linkage of a handcuff or shackle to be received; where they are joined to produce a seam satisfying the mechanical requirements of a physical restraint, further in the process of joining the top rear edge and top front edge, a front side and a rear side are formed that are of a substantially similar geometry, excepting those areas on the rear side set out to accommodate the attachment of wrist retaining straps, whereby the front side and rear side are joined at their respective first edge and second edge, and having a partition seam that traverses from a midline of a base of fabric pouch; which is the point wherein the demarcation of the front side and the rear side occurs; to a predetermined location in the proximity of the top rear edge and top front edge while simultaneously joining the front side and the rear side, wherein the partition seam terminates in a "T" shape; when viewed from the front perspective plane and providing for adequate accommodation of the linkage of a handcuff or shackle to be received, thereby forming a septum within the soft hand restraint device that serves to separably secure the hands together of a restrained individual in a thumb-to-thumb orientation within the plane formed by the first and second sides of the soft hand restraint device while simultaneously preventing the restrained individual from using his hands to grasp objects or individuals, wherein the area within the septum is further configured by stitched splay seams in a predetermined shape to accommodate the pairing of the index and middle finger and the ring and small finger in pockets that splay these two pairs of fingers at a predetermined angle, at least one retaining clip mechanism, comprising a spring latch closure having a male lead having at least one tensional element that is received in a corresponding female receptacle wherein, the male lead and the female receptacle further provide a means for the respective attachment of a male lead attachment strap and female receptacle attachment strap, which respectively comprise a material of construction having durability and strength commensurate with the demands of transporting prisoners, wherein the male lead is attached by the male lead attachment strap to the front side and is received in the female receptacle, which is attached by the female receptacle attachment strap to a handcuff retainer;

at least two wrist retaining straps, comprising a rectangular shaped flexible material of a predetermined size, having a first side, a second side, a top edge, a bottom edge, an attachment area, a wrist retaining strap hook fastener and a wrist retaining strap loop fastener, wherein the wrist retaining strap hook fastener has a predetermined shape and substantially similar dimensional characteristics of the wrist retaining strap first side to which it is affixed, and the wrist retaining strap loop fastener is of a predetermined shape and substantially similar dimensional characteristics of the wrist retaining strap second side to which it is affixed, wherein the wrist retaining straps are joined about the midsection of this construction in an area bordering the top edge and the bottom edge that may range to the width of the tabs formed in the fabric pouch top rear edge comprising an attachment area whereby the wrist retaining straps are joined in matched agreement with the tabs formed in the fabric pouch top rear edge;

a handcuff retainer which is joined to the soft hand restraint rear side about the midline near the top rear edge, comprising a rectangular shaped flexible material of a predetermined size, having a first side, a second side, a top edge, a bottom edge, an attachment area, a handcuff retainer hook fastener and handcuff retainer loop fastener, wherein the handcuff retainer hook fastener is affixed to the handcuff retainer first side further comprises a predetermined shape and substantially similar dimensional characteristics of the handcuff retainer less the predetermined area of attachment area, which comprises an area about the midsection of the first side bordered by the top edge and the handcuff retainer hook fastener that ranges to the width of the handcuff retainer wherein the handcuff retainer is secured to the fabric pouch; the handcuff retainer loop fastener is located about the midline of the soft hand restraint front side so as to engage the handcuff retainer hook fastener when it is drawn over the fabric pouch top rear and front edges, the handcuff retainer second side is secured about the midsection to the female receptacle attachment strap whereby the retaining clip mechanism female receptacle is connected, a plurality of restraint grommets comprising any waterproof, corrosion resistant grommet of a predetermined size of construction capable of penetrating heavy fabric with adequate flange width to resist pullout and compromise of the fabric while presenting a smooth rounded edge to any binding devices exposed to the grommet; being further capable of enduring the rigors anticipated in transporting prisoners; the restraint grommets are situated at predetermined locations about the fabric pouch in the general proximity of the fabric pouch top front edge and the handcuff retainer on the fabric pouch front side, wherein a corresponding restraint grommets are located on the fabric pouch rear side, and a plurality of D-rings comprising a waterproof, corrosion resistant D-ring of a predetermined size having of construction capable of being secured to heavy fabric with an adequate bearing surface width to resist pullout and compromise of the fabric while presenting a smooth rounded edges to any binding devices exposed to the D-ring; being further capable of enduring the rigors anticipated in transporting prisoners; the restraint D-rings being situated at predetermined locations about the fabric pouch in the general proximity of the fabric pouch top front edge, bottom edge, first side edge, second side edge and about the handcuff retainer on the fabric pouch front side, wherein corresponding D-rings are located on the fabric pouch rear side, all of which provide for the attachment of shackles, waist chains and also provide for securing the fabric pouch about the prisoner's thighs to further restrict the use of the prisoner's arms.

2. The soft hand restraint device for transporting prisoners of claim 1 further comprising a splay device situated in the immediate proximity of the splayed area of the paired fingers formed by the stitched splay seams, which comprises a means for maintaining a predetermined tension and splay angle, which is selected from a group consisting of rigid polymeric wedges, chevron shaped metallic inserts, non-deformable plastic chevron shaped inserts and a combination thereof.

3. The soft hand restraint device of claim 2, wherein said splay angle comprises a range from 30 to 90 degrees, inclusive.

4. The soft hand restraint device of claim 3, wherein said reinforcement splay is detachably attached in the fabric pouch such that the interior surface of the bag prevents direct contact with the hands of a prisoner.

5. The soft hand restraint device of claim 3, wherein said reinforcement splay is permanently affixed in the fabric pouch such that the interior surface of the bag prevents direct contact with the hands of a prisoner.

6. The soft hand restraint device of claim 2, wherein said splay device further comprising a reinforcement splay.

7. The soft hand restraining device for transporting prisoners of claim 2 further comprising a thumb adduction device within the septum is further configured by stitched splay seams in a predetermined shape to accommodate the pairing of the thumb, index and middle finger and the ring and small finger in pockets that splay these two pairs of fingers at a predetermined angle.

8. The soft hand restraining device for transporting prisoners of claim 7, wherein the thumb adduction device comprises a means for maintaining the proximal metacarpal of the thumb in rigidly adducted compliance with the index finger proximal phalange, wherein the means is selected from a group consisting of predetermined shapes comprising rings, saddles, clips and sleeves that arrest the motion of the thumb through the application of tensional forces.

9. The soft hand restraint device of claim 8, wherein the thumb adduction device may be constructed from a material of construction selected from a group consisting of metal, non-deformable polymers, fiberglass and combinations thereof.

10. The soft hand restraint device of claim 8, wherein the thumb adduction device is permanently affixed in the fabric pouch such that the interior surface of the bag prevents direct contact with the hands of a prisoner.

11. The soft hand restraint device of claim 8, wherein the thumb adduction device is detachably attached in the fabric pouch such that the interior surface of the bag prevents direct contact with the hands of a prisoner.

* * * * *